(12) United States Patent  (10) Patent No.: US 8,105,088 B2
Charles  (45) Date of Patent: *Jan. 31, 2012

(54) HEALTH MANAGEMENT CUFF

(76) Inventor: Chelsea Charles, Cordova, TN (US)

(*) Notice: Subject to any disclaimer, the term of this patent is extended or adjusted under 35 U.S.C. 154(b) by 316 days.

This patent is subject to a terminal disclaimer.

(21) Appl. No.: 12/370,089

(22) Filed: Feb. 12, 2009

(65) Prior Publication Data
US 2009/0162816 A1  Jun. 25, 2009

Related U.S. Application Data

(63) Continuation-in-part of application No. 11/600,371, filed on Nov. 16, 2006, now abandoned, which is a continuation-in-part of application No. 10/951,152, filed on Sep. 27, 2004, now Pat. No. 7,153,138.

(60) Provisional application No. 60/506,542, filed on Sep. 26, 2003.

(51) Int. Cl.
G09B 19/00 (2006.01)

(52) U.S. Cl. ........................................ 434/127

(58) Field of Classification Search .................. 434/127, 434/203, 204, 236, 246; 63/38, 40; 235/61 R, 235/123, 1 B
See application file for complete search history.

(56) References Cited

U.S. PATENT DOCUMENTS

| 1,124,518 | A | * | 1/1915 | Qvarnstrom | 24/115 H |
| 2,937,459 | A | * | 5/1960 | Belfield | 434/246 |
| 2,992,495 | A | | 7/1961 | Perreira | |
| 3,347,037 | A | * | 10/1967 | Klang | 63/21 |
| 4,599,508 | A | | 7/1986 | Smetaniuk | |
| 4,912,307 | A | | 3/1990 | Shade et al. | |
| 4,912,944 | A | | 4/1990 | Crosley et al. | |
| 4,965,553 | A | | 10/1990 | DelBiondo, II et al. | |
| 4,993,952 | A | | 2/1991 | Yeh | |
| 5,338,202 | A | | 8/1994 | Saari | |
| 5,382,165 | A | | 1/1995 | Knox | |
| 5,412,560 | A | | 5/1995 | Dennison | |
| 5,451,079 | A | | 9/1995 | Gong et al. | |
| 5,796,640 | A | | 8/1998 | Sugarman et al. | |
| 5,890,128 | A | | 3/1999 | Diaz et al. | |
| 5,915,854 | A | | 6/1999 | Burke et al. | |
| 6,065,971 | A | | 5/2000 | Lennon | |
| 6,223,559 | B1 | | 5/2001 | Coleman | |
| 6,279,958 | B1 | | 8/2001 | Santa Cruz et al. | |
| 6,341,295 | B1 | | 1/2002 | Stotler | |
| 6,431,873 | B1 | | 8/2002 | Flagg | |
| 6,478,736 | B1 | | 11/2002 | Mault | |
| 6,557,376 | B2 | * | 5/2003 | Pratt | 63/3 |
| 6,561,415 | B2 | | 5/2003 | Grant | |
| 6,561,514 | B2 | * | 5/2003 | Myles | 273/292 |

(Continued)

OTHER PUBLICATIONS

International Search Report for PCT/US2010/022600.

Primary Examiner — Kurt Fernstrom
(74) Attorney, Agent, or Firm — Howard & Howard Attorneys PLLC

(57) ABSTRACT

A cuff for a health managing system includes a strand having first and second terminal ends. A plurality of beads, each presenting a numerical or a non-numerical value, are slidably retainable and movable along the strand. The beads are movable between various positions between the first and second terminal ends for tabulating a health management system or preventing movement of the beads between the first and second terminal ends.

18 Claims, 2 Drawing Sheets

U.S. PATENT DOCUMENTS

| | | |
|---|---|---|
| 6,569,039 B1 | 5/2003 | Cope |
| 6,626,757 B2 | 9/2003 | Oliveras |
| 6,901,771 B2 * | 6/2005 | Ooide .............................. 63/26 |
| 7,300,286 B2 | 11/2007 | Palang |
| 7,540,172 B2 * | 6/2009 | Julkowski et al. ................. 63/3 |
| 2001/0043664 A1 | 11/2001 | Grant |
| 2002/0055087 A1 | 5/2002 | Hardesty |
| 2005/0069844 A1 | 3/2005 | Charles |
| 2005/0282127 A1 | 12/2005 | Adams |
| 2006/0230786 A1 | 10/2006 | Mishima |

\* cited by examiner

HEALTH MANAGEMENT CUFF

RELATED APPLICATIONS

This application is a Continuation-In-Part application of the U.S. patent application Ser. No. 11/600,371 filed Nov. 16, 2006, which is a Continuation-In-Part application of the U.S. patent application Ser. No. 10/951,152 filed Sep. 27, 2004, now U.S. Pat. No. 7,153,138, all of which are incorporated herewith by reference in their entirety.

FIELD OF THE INVENTION

The subject invention relates generally to an accessory item and, more particularly, to a dieting aid or a dieting system inclusive of a calorie-counting bracelet.

BACKGROUND OF THE INVENTION

Today, people are heavier than ever before. Poor diet and physical inactivity, two major contributors to obesity, are closing in on tobacco use as the leading preventable causes of death in the United States, according to a report in March in the Journal of the American Medical Association. Also, since people place so much emphasize on appearance, often added pounds create a negative self-image resulting in depression and an overall lack of motivation to better their lives. When the money spent attempting to fix the health-related damages of obesity is added with that spent on our society's constant desire to be svelte, it equals a multi-billion dollar weight-loss industry. People will go to extremes to lose weight; attempting things like, juice fasts, life-threatening diet pills, fad diets, and exercise binges.

But, despite the miracle-promising weight loss scheme introduced each day, people continue to gain weight at an alarming rate. Usually two things happen when they embark on the fad diet. First thing relates to loss of interest because the diet method or tool cannot fit into their everyday lives. Second, even if weight is lost, it eventually returns with a vengeance due to boredom or exhaustion with the weight-loss tool and/or program. So despite the miracle promises, the only proven, sure ways to lose weight and keep it off are a combination of exercises and combined monitoring of both calorie and carbohydrate consumption. Fitness experts recommend keeping a food diary to write down everything, as soon as it is consumed. There are also software programs and electronic adding machines to count the number of calories if one knows the content of the items consumed. Unless there is a visible, constant reminder throughout the day, these tools won't be utilized. In order for a weight loss tool to be successful in this fast-paced, image-driven society it must adapt to people of different lifestyles and fashion tastes, at different stages of their lives; promote health and discipline without resulting in extreme deprivation.

Various dieting devices and methods have been taught by the U.S. Pat. Nos. 5,338,202 to Saari; 5,382,165 to Knox; 5,915,854 to Burke et al.; 5,796,640 to Sugarman et al.; and 6,341,295 to Stotler. One such example, disclosed in the U.S. Pat. No. 5,338,202 to Saari, teaches a planner having a foldable carrying case with a plurality of pockets and pocket inserts, or meal insert cards on and in the inside walls of the carrying case. Each meal insert cards identifies a specific meal type such as, for example, a dinner or a breakfast. A plurality of food cards each listing one specific food within a food exchange and displaying a picture of either the approximate or visual serving size of the food. A user selects the food cards each listing one specific food and places them in the pockets for the type of the meal. One of the prime shortcomings of the aforementioned calorie counting devices is their unattractiveness and blatant purpose. Most people today simply do not want to advertise the fact that they are dieting, let alone wear an unattractive numeric-indicator or planner for displaying the thousands of calories consumed in a day.

Alluding to the above, a bracelet, taught by the U.S. Pat. No. 6,561,415 to Grant, tried to solve the aforementioned problem. The bracelet includes sliding attached beads, intermittent "summing" beads, and a printed plastic wallet card that indicates the bead values for commonly eaten foods. The beads are assigned a value of 100 calories per bead and are subdivided into groups of summing beads. For every 100 calories consumed, one bead is moved across the bracelet. The bracelet taught by the U.S. Pat. No. 6,561,415 to Grant does not prevent the backwards and/or forward movement of beads, which results in uncontrolled movement of the beads through strenuous exercise or daily routine. In addition, the bracelet is unattractive and does not work with every type of outfit for a variety lifestyles. In addition, a tracking space defined between the beads is about half on an inch, which results in an unpleasantly looking bracelet.

But even, if it is practicable, it would be desirable to provide an improved bracelet or a cuff that fully prevents the backwards and/or forward movement of beads, thereby controlling "bead slide" created by through strenuous exercise or daily routine. It would also be beneficial to present an attractive accessory to work with every type of outfit for variety of lifestyles.

SUMMARY OF THE INVENTION

A health management cuff of the present invention includes a strand having first and second terminal ends. A plurality of beads are retained on the strand and are slidably movable between the first and second terminal ends. A ring is integral with and extends from the strand presenting a dividing segment thereby dividing the strand into opposing strand sections and providing a difference in resistance to movement of the plurality of beads along the opposing strand sections from the dividing segment, thereby retaining the plurality of beads on one of the opposing strand sections.

Alluding to the above, each bead defines an inner surface having a layer of elastomeric material connected to the inner surface. The layer of elastomeric material is compressed as the bead is moved over the dividing element from the first terminal end to the second terminal end and expands to frictionally engage the strand as the bead is moved beyond the dividing element. The elastomeric material may include a rubber made from silicone elastomers noted for its retention of flexibility, resilience, and tensile strength over a wide temperature range.

An advantage of the present invention is to provide the cuff which is attractive and fits with every type of outfit for individuals' varying lifestyles.

Another advantage of the present invention is to provide the cuff which is a cost-effective, safe, and simple tool created to aid weight-loss and style for people of all ages.

Still another advantage of the present invention is to provide a health cuff or bracelet adaptable to count glasses of water, fruit/vegetable servings, golf swings, and the like.

Still another advantage of the present invention is to provide a health cuff or bracelet adaptable to be used to monitor emotional and spiritual wellness goals, such as blessings, prayers, kind words, kind deeds, 12 step programs, service hours, hugs, moments of controlled anger, motivational thoughts, accomplishments.

DESCRIPTION OF THE INVENTION

Figure 1:
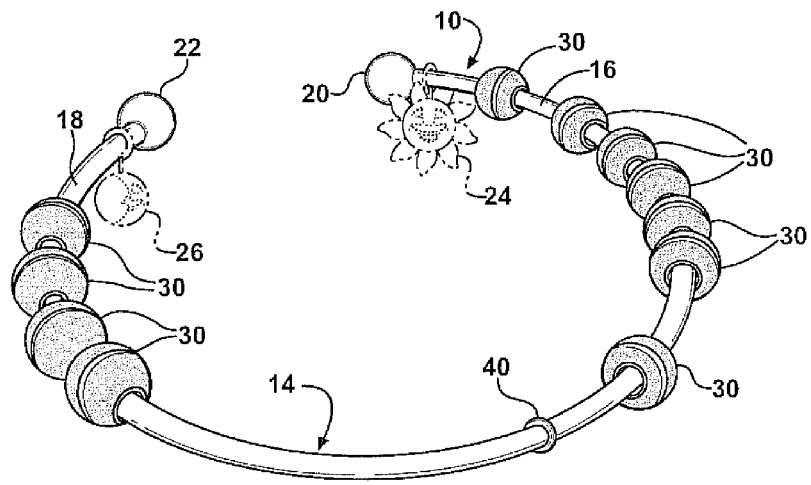
FIG. 1 shows a health management cuff including a strand and a plurality of beads and a ring circumscribing the strand of the cuff for controlling movement of the beads along the strand.

Referring to FIG. 1, an inventive health management cuff for a health management system is generally shown at 10. The cuff 10 includes a strand, generally indicated at 14 having first 16 and second 18 strand sections each presenting terminal ends 20 and 22, respectively. Preferably, the first and second strand sections 16 and 18 present a circular configuration. However, other configurations of the strand 14 are contemplated by the present invention. Preferably, each first and second strand sections 16 and 18 may include a charm bead, 24 of one kind, as shown in phantom, identifying a first part (A.M.) of a day and a charm bead of another kind 26, also shown in phantom, identifying a second part (P.M.) of the day. Both charm beads 24 and 26 are mechanically disposed at the respective terminal ends 20 and 22 to assist a user (not shown) in tabulating the health managing system when counting intake of the calories, or, for example, when taking a medicine.

Figure 2:
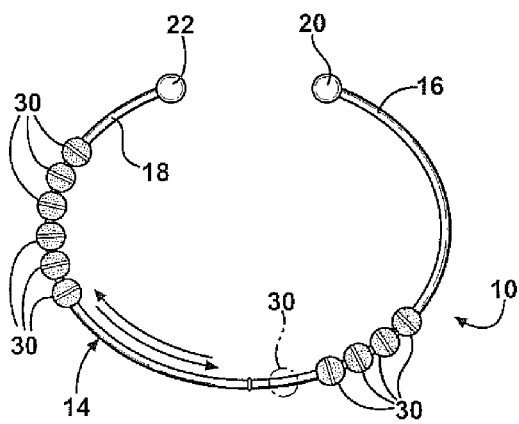
FIG. 2 shows the health management cuff of FIG. 1 with an arrow pointing to the direction of the movement of the beads along the strand.
Figure 3:
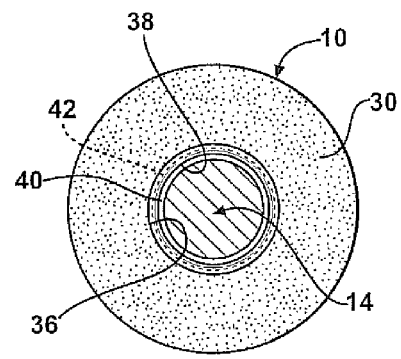
FIG. 3 shows a cross sectional view of the bead having a layer of elastomeric material circumscribing the strand.

As best shown in FIG. 2, a plurality of beads 30 or charms are retained along the strand 14 and are movable between the first and second strand sections 16 and 18. Preferably, the number of beads 30 is twenty to form the aforementioned health managing system, wherein each bead 30 signifies a fragmental numerical or non-numerical value of the health managing system. Alternatively, the number of beads 30 may be adjusted as the user may desire. For example, each bead 30 signifies 100 calories or a number of carbohydrates, depending on what phase the user is at his/her diet. As shown in FIGS. 3 and 4, each bead 30 includes a wall 32 defining an opening 34 adaptable to receive the strand 14 extending therethrough. An inner surface 36 of the bead 30 receives a layer of an elastomeric material 38. Preferably, each bead 30 presents a round configuration, as shown in FIGS. 1 through 4. Alternatively, each bead 30 may present a form of a cube, a cylinder, or the like (not shown). Each bead 30 may be formed from a metal, a polymer, a wood, or the like.

Figure 4A:
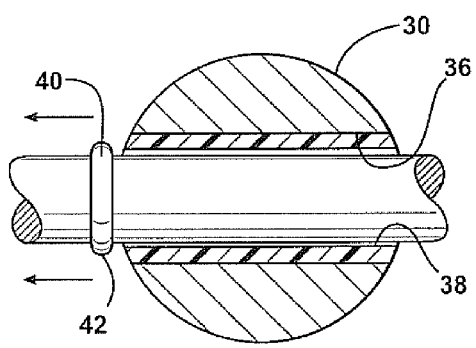
FIG. 4A shows another cross sectional view of the bead in a first position before the bead is moved over the ring of the strand from a first end of the strand to the second end of the strand.
Figure 4B:
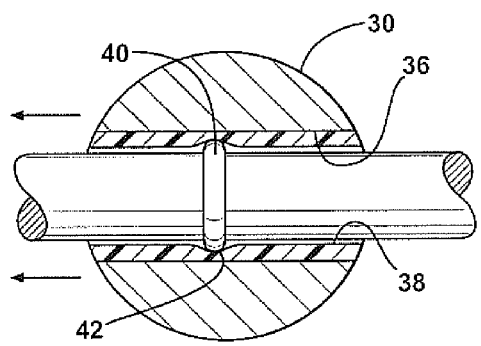
FIG. 4B shows another cross sectional view of the bead in a second position with the ring of the strand elastically deforming a layer of elastomeric material surrounding the inner surface of the bead as the bead is moved from the first end of the strand to the second end of the strand.

Referring back to FIGS. 1 through 4B, a dividing segment defined by a ring, generally indicated at 40 is disposed between first and second strand sections 16 and 18. The ring 40 is integrally formed with and extends outwardly from the strand 14. The ring 40 presents a semi-circular end portion 42. The end portion 42 may present a non-circular configuration without limiting the scope of the present invention. As best illustrated in FIGS. 3, 4A and 4B, the bead 30 is movable between a first position, i.e. a sliding position, and a second position, i.e a blocking position. The layer of elastomeric material 38 is compressed as the bead 30 is moved over the ring 40 from the first strand section to the second strand section 18 wherein the ring 40 forces the layer 38 to the inner surface 36 of the bead 30, as shown in FIG. 4B. The layer 38 expands to its normal, i.e. pre-compressed position, as the bead 30 is moved beyond the ring 40 as shown in FIG. 4A.

Typically, the user counts calories ingested based on assigned quantitative caloric values of each bead 30. Once food is ingested, the user slides the appropriate number of beads 30 from the first terminal end 16 to the second terminal end 18 of the cuff 10 for later count. At the end of the day, the user sums the total calories ingested through enumeration of beads 30 slid from one of the terminal end 16 of the cuff 10 to another terminal end 18 as compared with their assigned quantitative values. Finally, the user moves the counting beads 30 back to their original position to begin counting the next day. The cuff 10 may include a male connector and female connectors, not shown, at each connected to the first and second terminal ends 16 and 18 to mechanically engage the terminal ends 16 and 18 to form a loop. Such male and female connectors are further defined by a pair of opposite jump rings, known to those skilled in the art, to provide a convenient means of attachment between the first and second terminal ends 16 and 18.

The layer of elastomeric material 38 is typically tacky and may be a gel, gum, liquid, paste, resin, or solid and may be cured or uncured. In one embodiment, the layer of elastomeric material 38 is a film. In another embodiment, the layer of elastomeric material 38 is a gel. In yet another embodiment, the layer of elastomeric material 38 is a liquid that is cured to form a gel. The layer of elastomeric material 38 may include silicon (Si) atoms (e.g. silanes, siloxanes, silazanes, etc) and/or be further defined as a silicone. As is well known in the art, silicones are typically defined as mixed inorganic-organic polymers (i.e., polyorganosiloxanes) that include a polymerization product of one or more siloxane monomers that include $R_2SiO$ units wherein each R is a hydrogen atom or a hydrocarbon group. Siloxane monomers may also have branched or unbranched backbones of alternating silicon and oxygen atoms (—Si—O—Si—O—) with organic or inorganic side chains attached to the silicon atoms.

In various embodiments, the layer of elastomeric material 38 is further defined as the polymerization (e.g. cured) product of organosilanes, organosiloxanes, polyorganosilanes, polyorganosiloxanes, silicone acrylates, or combinations thereof. The organosilanes, organosiloxanes, polyorganosilanes, polyorganosiloxanes, and silicone acrylates may be cured by any means known in the art including, but not limited to, free radical curing, hydrosilylation curing, and condensation curing.

In one embodiment, the layer of elastomeric material 38 includes the polymerization product of a polyorganosiloxane, first introduced above. The polyorganosiloxane may have the following average unit formula: $(R'_3SiO_{1/2})_x(R'_2SiO_{2/2})_y(R'SiO_{3/2})_z$ wherein x and y are positive numbers, z is greater than or equal to zero, and at least one R' includes a polymerizable group. As is well known in the art, polyorganosiloxanes typically have the following structures: wherein each of M, D, T, and Q independently represent functionality of structural groups of polysiloxanes. Specifically, M represents a monofunctional group $R_3SiO_{1/2}$. D represents a difunctional group $R_2SiO_{2/2}$. T represents a trifunctional group $RSiO_{3/2}$. Q represents a tetrafunctional group $SiO_{4/2}$. The polyorganosiloxane may include MQ resins including $R_3SiO_{1/2}$ groups and $SiO_{4/2}$ groups, TD resins including $RSiO_{3/2}$ groups and $R_2SiO_{2/2}$ groups, MT resins including $R_3SiO_{1/2}$ groups and $RSiO_{3/2}$ groups, MTD resins including $R_3SiO_{1/2}$ groups, $RSiO_{3/2}$ groups, and $R_2SiO_{2/2}$ groups, and combinations thereof. In each of these resins, R may be selected from the group of aliphatic, cylcoaliphatic, and aromatic moeities.

It is also contemplated that the polyorganosiloxane may be selected from the group of polydimethylsiloxane, α,$\overline{\omega}$-methacryloxymethyldimethylsilyl terminated polydimethylsiloxane, methacryloxypropyl-terminated polydimethylsiloxane, α,$\overline{\omega}$-acryloxymethyldimethylsilyl terminated polydimethylsiloxane, methacryloxypropyldimethylsilyl terminated polydimethylsiloxane, α,$\overline{\omega}$-acryloxypropyldimethylsilyl terminated polydimethylsiloxane, poly(acryloxypropyl-methylsiloxy), polydimethylsiloxane and poly(methacryloxypropyl-methylsiloxy) polydimethylsiloxane copolymers, telechelic polydimethylsiloxanes having multiple acrylate or methacrylate functional groups, and combinations thereof.

The layer of elastomeric material 38 may also include polyorganosilanes which typically include a polymerization product of one or more silane monomers that include Si—H bonds. More specifically, the layer of elastomeric material 38 may include the polymerization product of an organosilane having the general structure: $R_nSi(OR')_{4-n}$ wherein n is an integer of less than or equal to 4 and wherein at least one of R and R' independently includes the free radical polymerizable group. Of course, it is to be understood that the above description of silicones containing silicon atoms is not limiting and that the instant layer of elastomeric material 38 may include any silicone or silicon chemistry known in the art.

Figure 5:
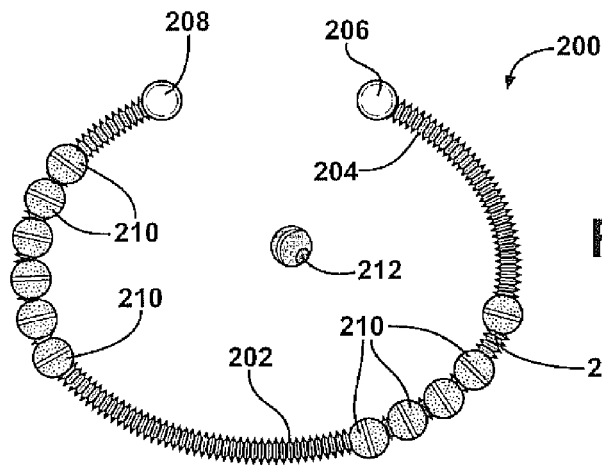
FIG. 5 shows an alternative embodiment of the present health management cuff.

FIG. 5 shows an alternative embodiment of the health management cuff or bracelet, generally shown at 200. The bracelet 200 includes a strand 202 presenting a first connector 204 defined by a thread formed in the strand 202 and extending from a first end 206 of the strand to a second end 208. A plurality of beads 210 are moveable between the first end 206 to the second end 208. Each bead 210 includes a second connector 212 defined therein. The first and second connectors 204 and 212 are meshingly engaged with one another thereby allowing the user to move the beads 210 along the strand 202 as the beads 210 are rotated by the user about the strand 202. The beads 210 are stayed in a fixed position if not moved by the user.

Figure 6:
FIG. 6 shows another embodiment of the bead.

FIG. 6 shows an alternative embodiment of a bead 300 having a first portion 302 and a second portion 304 hinged 306 with one another to allow the portions 302 and 304 to be engaged with one another by a locking mechanism 308 as the bead is on the strand 310 and to be disengaged if the used wants to remove the bead 300 or add additional bead 300 to the strand 310. A dividing segment defined by a ring 311 is disposed on the strand 310. The ring 311 is integrally formed with and extends outwardly from the strand 310. An inner surface of the bead 300 may include a layer of an elastomeric material as previously discussed.

Figure 7:
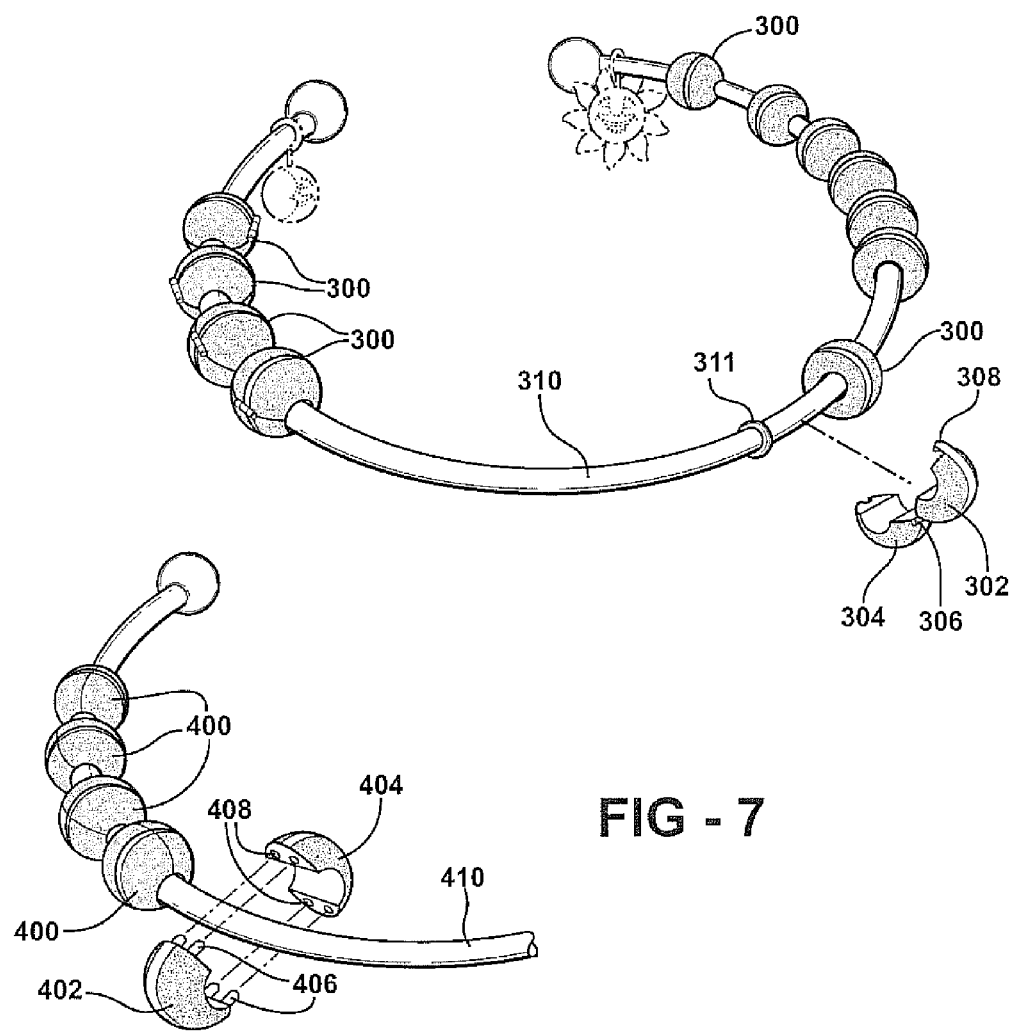
FIG. 7 shows yet another alternative embodiment of the bead.

FIG. 7 shows yet another alternative embodiment of a bead 400 having a first portion 402 and a second portion 404 connected with one another by male connectors 406 extended from the first portion 402 and engaged with female connectors 408 defined in the second portion 404 to allow the portions 402 and 404 to be engaged with one another as the bead 400 is on the strand 410 and to be disengaged if the user wants to remove the bead 400 or add additional bead 400 to the strand 410. Those skilled in the art will appreciate that numerous other configurations of the male connectors 406 and the female connectors 408 may be utilized with the present invention and the connectors 406 and 408, shown in FIG. 7, are not intended to limit the scope of the present invention.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A health management cuff comprising;
   a strand having a first terminal end and a second terminal end,
   a plurality of beads retained on said strand moveable along said strand between said first terminal end and said second terminal end:
   each of said beads defining an inner surface having a layer of elastomeric material connected to said inner surface, said beads are movable between said first terminal end and said second terminal end in response to the external impact upon said beads; and
   a dividing element dividing said first terminal end and said second terminal end into opposing sections; said dividing element providing a difference in resistance to movement of said beads between said opposing sections thereby retaining said beads proximate said first terminal end or said second terminal end.

2. A health management cuff as set forth in claim 1 wherein said dividing element is further defined by a ring being integral with and extending from said strand.

3. A health management cuff as set forth in claim 2 wherein said inner surface of each bead presents a wall defining an opening for receiving said strand.

4. A health management cuff as set forth in claim 3 wherein said elastomeric material is further defined by polymeric organic silicon.

5. A health management cuff as set forth in claim 2 wherein said elastomeric material is compressed as said bead is moved over said ring from said first terminal end to said second terminal end and expands to frictionally engage said strand as said bead is moved beyond said ring.

6. A health management cuff as set forth in claim 4 wherein said strand is formed from a metal.

7. A health management cuff as set forth in claim 6 wherein each bead signifies a fragmental value of a health management system.

8. A health management cuff comprising;
   a strand having first and second terminal ends and a dividing element extending from said strand separating said first terminal end from said second terminal end,
   a plurality of beads retained on said strand moveable along said strand between said first terminal end and said second terminal end with each of said beads defining an inner surface having a layer of elastomeric material connected to said inner surface, and said layer of elastomeric material being compressed as said bead is moved over said dividing element from said first terminal end to said second terminal end thereby increasing the resistance to movement of said bead and expanding to frictionally engage said strand as said bead is moved beyond said dividing element thereby returning the resistance to movement to its original resistance; said dividing element retaining said bead proximate either said first terminal end or said second terminal end.

9. A health management cuff as set forth in claim 8 wherein said dividing element is further defined by a ring being integral with and extending from said strand.

10. A health management cuff as set forth in claim 9 wherein said inner surface of each bead presents a wall defining an opening for receiving said strand.

11. A health management cuff as set forth in claim 10 wherein said elastomeric material is further defined by polymeric organic silicon.

12. A health management cuff as set forth in claim 11 wherein said strand is formed from a metal.

13. A health management cuff as set forth in claim 12 wherein each bead signifies a fragmental value of a health management system.

14. A health management cuff comprising;
a strand having first and second terminal ends and a dividing element extending from said strand separating said first terminal end from said second terminal end,
a plurality of beads retained on said strand moveable along said strand between said first terminal end and said second terminal end with each of said beads defining an inner surface, and
a layer of polymeric organic silicon connected to said inner surface and being compressed as said bead is moved over said dividing element from said first terminal end to said second terminal end thereby increasing the resistance to movement of said bead from said second terminal end to said first terminal end and said layer of polymeric organic silicon expanding to frictionally engage said strand as said bead is moved beyond said dividing element to an original resistance to movement.

15. A health management cuff as set forth in claim 14 wherein said dividing element is further defined by a ring being integral with and extending from said strand.

16. A health management cuff as set forth in claim 15 wherein said inner surface of each bead presents a wall defining an opening for receiving said strand.

17. A health management cuff as set forth in claim 16 wherein said strand is formed from a metal.

18. A health management cuff as set forth in claim 17 wherein each bead signifies a fragmental value of a health management system.

\* \* \* \* \*